United States Patent [19]

Baroth et al.

[11] Patent Number: 5,307,096
[45] Date of Patent: Apr. 26, 1994

[54] COMPUTER DRIVEN OPTICAL KERATOMETER AND METHOD OF EVALUATING THE SHAPE OF THE CORNEA

[75] Inventors: Edmund C. Baroth, Granada Hills; Samih A. Mouneimme, La Canada, both of Calif.

[73] Assignee: California Institute of Technology, Pasadena, Calif.

[21] Appl. No.: 170,215

[22] Filed: Mar. 17, 1988

[51] Int. Cl.⁵ .............................................. A61B 3/10
[52] U.S. Cl. ................................... 351/212; 351/221
[58] Field of Search ........................ 351/212, 221, 246

[56] References Cited

U.S. PATENT DOCUMENTS 4,692,003  9/1987  Adachi et al. .................... 351/212
4,721,379  1/1988  L'Esperance ..................... 351/212

OTHER PUBLICATIONS

"Physicians & Computers", Leading Computer Health Care Journal, vol. 5, No. 4, Aug. 1987.

*Primary Examiner*—Paul M. Dzierzynski
*Attorney, Agent, or Firm*—Leonard Tachner

[57] ABSTRACT

An apparatus and method for measuring the shape of the cornea utilize only one reticle to generate a pattern of rings projected onto the surface of a subject's eye. The reflected pattern is focused onto an imaging device such as a video camera and a computer compares the reflected pattern with a reference pattern stored in the computer's memory. The differences between the reflected and stored patterns are used to calculate the deformation of the cornea which may be useful for pre-and post-operative evaluation of the eye by surgeons.

16 Claims, 5 Drawing Sheets

COMPUTER DRIVEN OPTICAL KERATOMETER AND METHOD OF EVALUATING THE SHAPE OF THE CORNEA

ORIGIN OF INVENTION

The invention described herein was made in the performance of work under a NASA contract, and is subject to the provisions of Public Law 96-517 (35 USC 202) in which the Contractor has elected to retain title.

TECHNICAL FIELD

The present invention relates generally to keratometry, that is, measurement of the cornea of the human eye and more specifically, to a laser keratometer having an optical subsystem designed to impose a reticle-generated series of rings on the eye and capture a series of reflected rings from the eye. A computer-stored reference image is effectively superimposed on the image reflected from the subject's eye so that computer processing provides means for generating either real time or near real time information on the eye shape.

BACKGROUND ART

Corneal surgery is currently undergoing rapid evolution with improvements designed to minimize or eliminate astigmatism following penetrating keraplasty (corneal transplants), as well as to correct refractive error. Because the cornea is the most powerful refracting surface of the eye, numerous procedures have been devised to incise, lathe, freeze, burn and reset the cornea to alter its shape. Currently practiced keratorefractive surgical techniques include: cryorefractive techniques (keratomileusis, keratophakia, ipikeratophakia), radialkeratotomy, thermal keratoplasty, corneal relaxing incisions and wedge resections.

When preparing the patient for any of these surgical techniques, it is essential to accurately measure the corneal curvature. Existing methods to measure corneal curvature include central keratometry and photokeratoscopy with central keratometry. However, with these methods only the central three millimeters of the cornea is measured. Recently, photokeratoscopy has been adapted to provide a topographic map of the cornea. However, this technique in its present form provides only a qualitative assessment of the cornea. This is because while photographs can be analysed by computer techniques or manual tracing, the time delay and effort in producing such data reduces the utility of the method for measuring corneal curvature preoperatively and for evaluating the effect of surgical techniques post-operatively. Thus, there is an ongoing need for a real time keratometer system for medical diagnosis and for preparation of the corneal contour for eye surgery as well as for post-operative analysis of completed eye surgery. One example of a computerized laser keratometer of the prior art utilizes a computer to analyse the moire patterns generated by laser excitation of the corneal surface and the resulting projecting and reflected beams. Unfortunately, such prior art devices have alignment problems as well as problems due to fringes that result from misalignment.

SUMMARY OF INVENTION

The system of the present invention provides a configuration that is somewhat similar to that of a classic keratometer, but with a novel optical system that illuminates through a shuttered light source and a focusing assembly and a sensor in the form of a solid state imager arranged to accept the image created by reflections from several zones of the cornea. A reference image is stored in a computer memory. The numerical superposition of the stored image on the reflected image from the subject's eye is displayed in real time or processed by the computer to yield numerical information regarding deformation of the eye. The novel approach of the present keratometer requires only one optical reticle which results in a substantial simplification in the optical system. Only the reflected ring pattern is required to be processed by the optical system. Since a reference reticle is generated and stored in the computer, the computer determines the center of the reflected ring pattern and overlays it precisely on the center of the reference ring pattern. Fringes due to misalignment are thus obviated in the present invention and only fringes due to deformation appear.

The present optical system imposes a series of rings generated by the reticle on the eye and captures a series of reflected rings. If no cornea deformation exists there is no displacement of the rings reflected from the eye from the reference set of rings stored in the computer. Any deformation causes some or all of the rings to be displaced slightly from the reference set and the computer determines the amount of deformation. In one particular embodiment disclosed herein, the apparatus comprises a helium-neon laser, a shutter, a reticle, a beam splitter, a quarter-wave plate and focusing assemblies. The reticle comprises a chrome deposited array of circular rings. Furthermore, in the particular embodiment disclosed herein the optical sensor or imager comprises a CCD video camera the output of which is eventually applied to a computer which is programmed to carry out the software routine disclosed herein for numerically analyzing the deformation of the observed cornea surface based upon displacement between the reflected image and the stored reference image.

OBJECTS OF THE INVENTION

It is therefore a principal object of the present invention to provide a computer driven optical keratometer as an evaluation tool for assessing the shape of the cornea primarily for pre-and post-operative evaluation in conjunction with corneal eye surgery.

It is an additional object of the present invention to provide a computer driven optical keratometer in which a reticle-induced series of rings is reflected off the surface of the cornea of the subject being tested and compared in a computer against a reference set of rings stored in the computer as a representation of a non-deformed corneal surface.

It is still an additional object of the present invention to provide a computer driven optical keratometer which may be advantageously used by opthamologists, optometrists and other such eye-related medical personnel for the purpose of evaluating the shape of the corneal surface and wherein a laser light source is used in conjunction with a single reticle pattern to produce a series of rings on the surface of the cornea which is reflected back into an optical focusing assembly and onto an optical sensor which transmits corresponding data to a computer which compares the reflected image with a stored reference image for evaluating the deformation of the cornea.

It is still an additional object of the present invention to provide a novel and advantageous method for numerically evaluating the shape of the cornea using only one reticle-generated ring pattern, the reflection of which is compared on a point-by-point basis with a stored reference pattern.

BRIEF DESCRIPTION OF THE DRAWINGS

The aforementioned advantages and objects of the present invention, as well as additional advantages and objects thereof, will be more fully understood hereinafter as a result of a detailed description of a preferred embodiment when taken in conjunction with the following drawings.

DETAILED DESCRIPTION OF THE INVENTION

Figure 1:
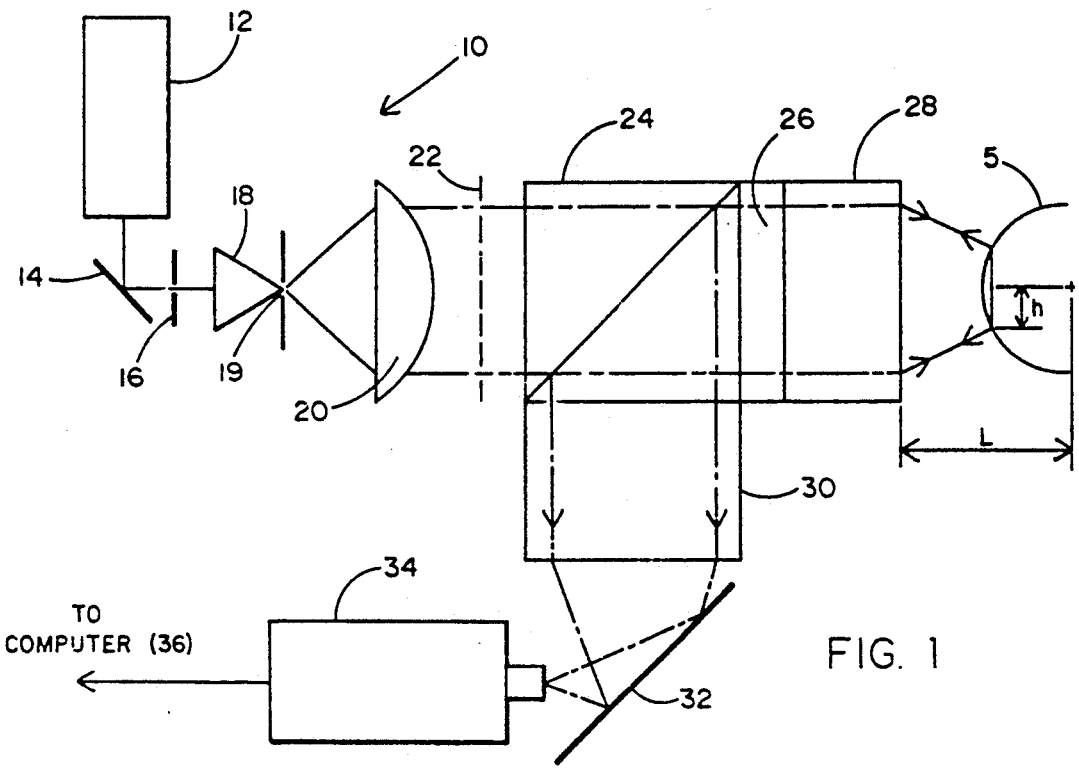
FIG. 1 is a block diagram representation of the optical subsystem of the present invention.
Figure 1A:
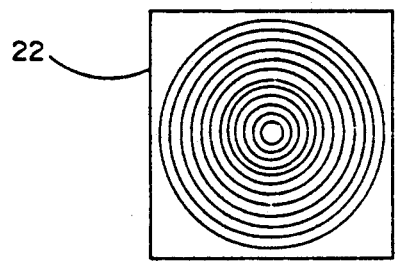
FIG. 1a illustrates the pattern of a reticle used in the preferred embodiment of the invention.

Referring now first to FIG. 1 it will be seen that the optical subsystem 10 of the present invention comprises a laser 12, a mirror 14, a shutter 16, a microscope objective lens 18, a pinhole 19, a collimating lens 20, a reticle 22, a beam splitter 24, a quarterwave plate 26, focusing assemblies 28 and 30, a mirror 32 and a video camera 34, the latter being connected to a computer 36. Although laser 12 may be any one of numerous lasers it has been found that it is preferable to use a laser operating in the visible light spectrum such as a helium-neon laser. Mirror 14 is be used to bend the light beam emitted by laser 12 so that it enters the microscope objective lens 18 along the proper optical path through a shutter 16. The shutter is designed to provide the optical subsystem with a pulse of laser light of the appropriate duration for the measurement and may be synchronized, by appropriate electronics (not shown), with the timing of computer 36. Objective lens 18 and pinhole 19 act in combination to provide a relatively narrow uniform light beam which is then appropriately shaped an redirected by collimating lens 20 to fill reticle 22 with a relatively intense, uniform light source in which all the rings of the reticle 22 (see FIG. 1a) receive roughly the same magnitude of incident light energy.

The rings of light produced by reticle 22 are transmitted through a beam splitter 24, a quarterwave plate 26 and a first focusing assembly 28 which focuses the rings on the eye 5 being measured over a selected circular region having a viewing radius h. The rings of light incident on the eye 5 are reflected by the surface of the cornea. The reflected light passes through focusing assembly 28, quarterwave plate 26 and enters beam splitter 24 where it is redirected at a 90 degree angle relative to the incident light path into focusing assembly 30. Focusing assembly 30 is designed to focus the reflected light or ring pattern onto mirror 32 which redirects the reflected light energy into the lens of video camera 34. Quarterwave plate 26 is designed to direct the light reflected from the eye 5 to the video camera by changing the polarization of the outgoing and incoming light by 90 degrees. The video camera 34 generates a corresponding signal replicating the reflected ring pattern from the eye 5 and transmits it to the computer 36. Electronics between video camera 34 and computer 36 may be used to configure the video camera electronic signal in an appropriate data output suitable for use by computer 36. The operation of the video camera 34 as well as the operation of any necessary electronics to configure the corresponding electrical signal to be compatible with a computer are well-known in the art and need not be disclosed herein in any detail.

As previously indicated, computer 36 is provided with a reference pattern, that is, with appropriate data corresponding to a set of reflected rings which would otherwise be received by video camera 34 if the corneal surface of the eye 5 were precisely spherical without any deformation whatsoever anywhere on its surface. It will be recognized that by simply altering the contents of the signal stored in the memory of computer 36, which signals correspond to the reference pattern to which the reflected pattern is compared by the computer, one can readily alter the reference pattern to any desired configuration. Thus, the optical system 10 of the invention imposes a series of rings generated by passage of light through a reticle onto the eye and captures a series of reflected rings reflected from the surface of the eye. If no deformation exists, then there is no displacement of the rings from a reference set stored in the computer. If there is deformation, it will cause some or all of the rings to be displaced slightly from the reference set and the computer determines the amount of such deformation. The computer numbers and locates the center of each ring and compares it to the corresponding reference ring. The output of computer 36 may be designed to provide different forms of information depending upon the application of the invention. Thus for example, computer 36 may be programmed to simply provide a read out in either diopters or millimeters of the relative radius of curvature of the cornea indicative of a refractive deficiency. On the other hand, computer 36 may be programmed to provide a detailed topographical map which may either be displayed in the form of a set of numerals or as an actual simulated presentation of the cornea shape. The first type of output of computer 36 may be readily used to correct a refractive deficiency of the eye, while the latter is preferable particularly for surgeons who wish to know precisely what the shape of the eye is before or after corrective surgery. Both types of computer outputs are generated in response to a detailed comparison between the reflected rings and the stored reference rings by computer 36 to determine the extent of corneal deformation. The program used in an embodiment of the invention that has been reduced to practice is designed to produce an output corresponding to the relative radius of curvature of the eye, but could be modified by those having skill in the relevant art to provide a topological map of the eye.

Reference will now be made to FIGS. 2-9 primarily to illustrate the method of the present invention and more specifically, to demonstrate by mathematical analysis at the interface of the rays of light and the real eye surface that the system of the present invention is capable of measuring deformations with necessary accuracy and resolution and to show that the reflected rings are sufficiently displaced by deformation to be analyzed by computer 36. Table I below defines the nomenclature used in FIGS. 2-9.

TABLE I

Figure 2:
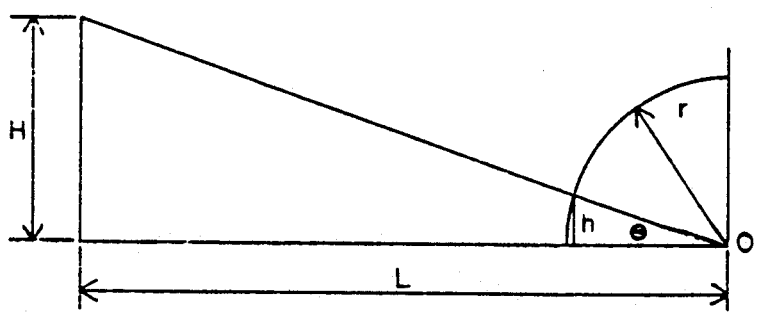
FIG. 2 is a schematic diagram of the final focusing lens of the optical system of FIG. 1 shown relative to the eye being measured.
Figure 3:
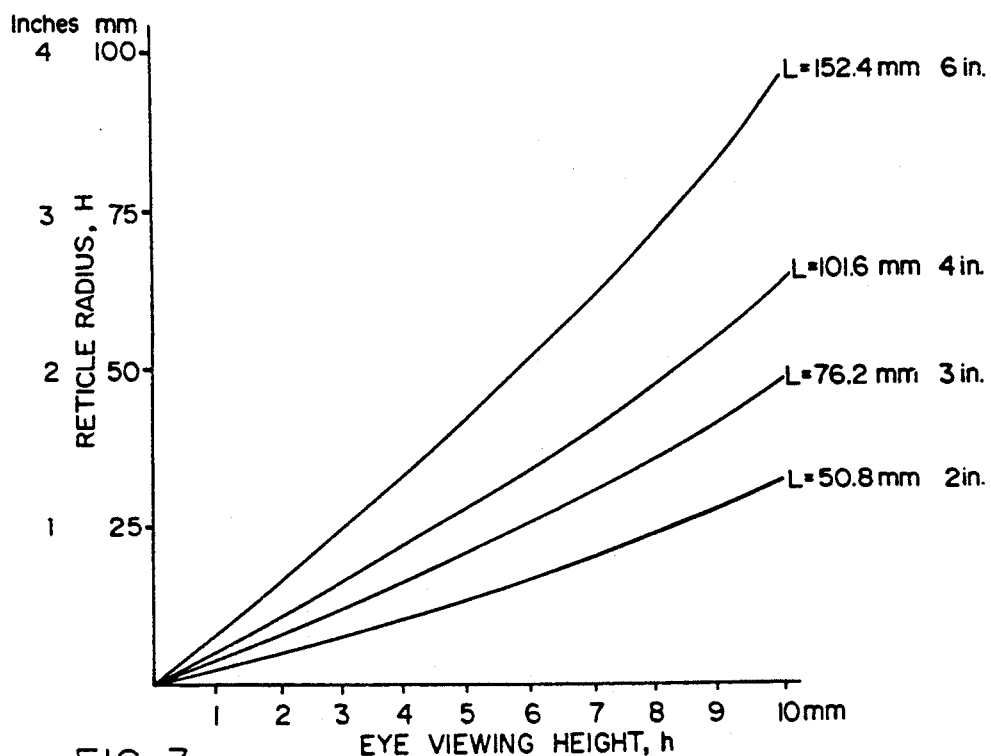
FIG. 3 is a graphical representation illustrating variation in reticle radius and eye viewing radius at various distances from the eye.

Nomenclature:
d = Spacing of rings on the eye, μm
h = Height above horizontal eye center for viewing (viewing radius), mm
$H_1$ = Height above central horizontal ray for Ring N, mm
$h_2$ = Height above central horizontal ray for Ring N+1, mm
H = Reticle radius, mm
l = Distance from center of eye to point where reflected ray intersects central horizontal ray, mm
L = Distance from edge of focusing lens to center of eye, mm
r = Radius of eye, assumed to be approximately .75 inch = 19.05 mm Points:
A - Intersection of N ring and radius of eye
B - Intersection of N+1 ring and radius of eye
D - Intersection of Real surface and horizontal line from point B
E - Intersection of Normal to line AD (from point F) and either line AB or BD
F - Intersection of Incident of ray of ring N+1 and real surface
G - Intersection of Reflected ray (from point F) and either line AB or AD
I - Intersection of Reflected ray projected back and central horizontal ray
M - Intersection of Reflected ray and focusing lens
O - Center of eye
P - Intersection of incident ray from ring N ring and focusing lens
Q - Intersection of incident ray from ring N+1 ring and focusing lens
S - Intersection of vertical projection down from point Q and central ray
T - Intersection of vertical projection down from point M and central ray Greek:
α = Angle between incident ray from ring N and central ray, Degrees
β = Angle between incident ray from ring N+1 and central ray, Degrees
γ = ½ (α+β), Degrees
δ = Difference between reference and actual points, measured horizontally, μm
Δ = Difference between incident and reflected rays, measured vertically, on focusing lens, mm
η = Angle between N+1 and N rings, Degrees
Θ = Total viewing angle, Degrees
ξ = Angle between reflected ray and incident ray at same point on focusing lens, Degrees TABLE I-continued Φ = Angle between reference normal and actual normal, Degrees FIG. 2 is a schematic diagram of the final focusing lens of focusing assembly 28 and the eye 5 being subjected to evaluation by the invention. FIG. 2 illustrates the lens at a distance L from the center of the eye. In order to view the exterior surface or cornea of the eye up to a height h from the central ray of the eye (represented by the horizontal line in FIG. 2), the lens radius must be at least height H. FIG. 3 is a graphical representation showing the variation of eye viewing height h with optical radius or reticle radius H for various distances between the final lens and the center of the eye. More specifically, the variation of h with H is shown for distances of 2, 3, 4 and 6 inches respectively. Thus it will be seen that in FIG. 3 that if, for a distance L of 4 inches between the center of the eye and the final lens of the focusing assembly, one desires an eye viewing height h of 8 millimeters, it is necessary to have a reticle or lens height of 50 millimeters. Precise dimensions for the optical section may be varied based on parameters such as cost and preferences of medical personnel.

Figure 4:
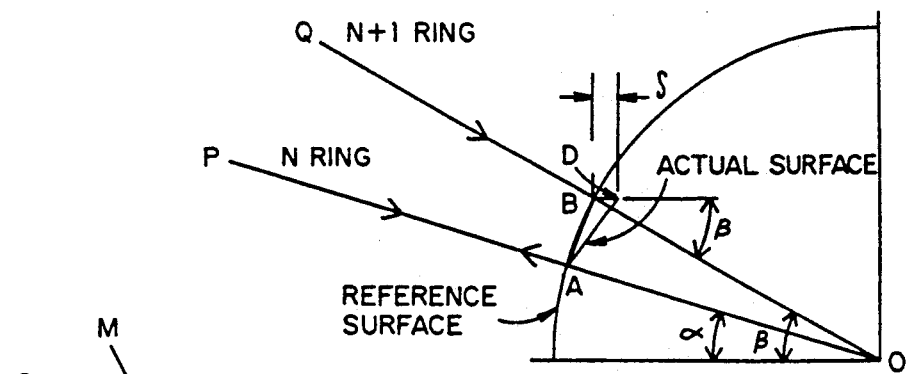
FIG. 4 is a schematic diagram illustrating the interrelationship between the eye being measured and rays emanating from the reticle.
Figure 4A:
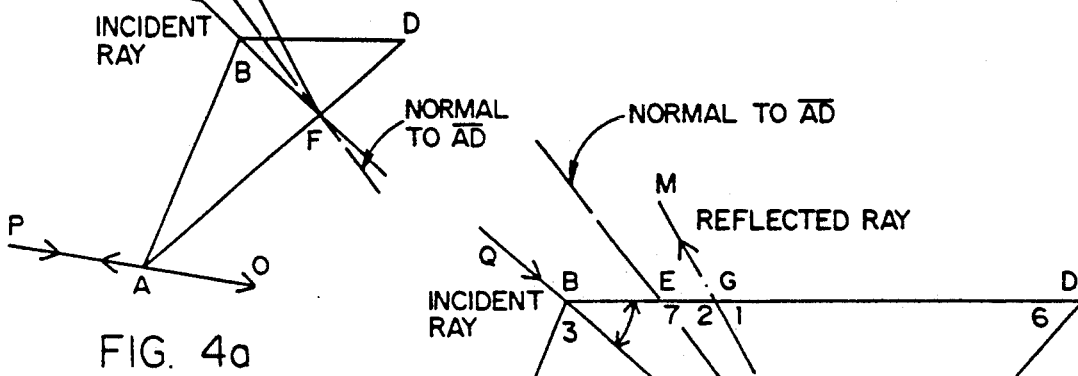
FIGS. 4a and 4b are two enlargements of a portion of FIG. 4 illustrating the mathematical analysis of the deformation measurement process of the present invention.
Figure 4B:
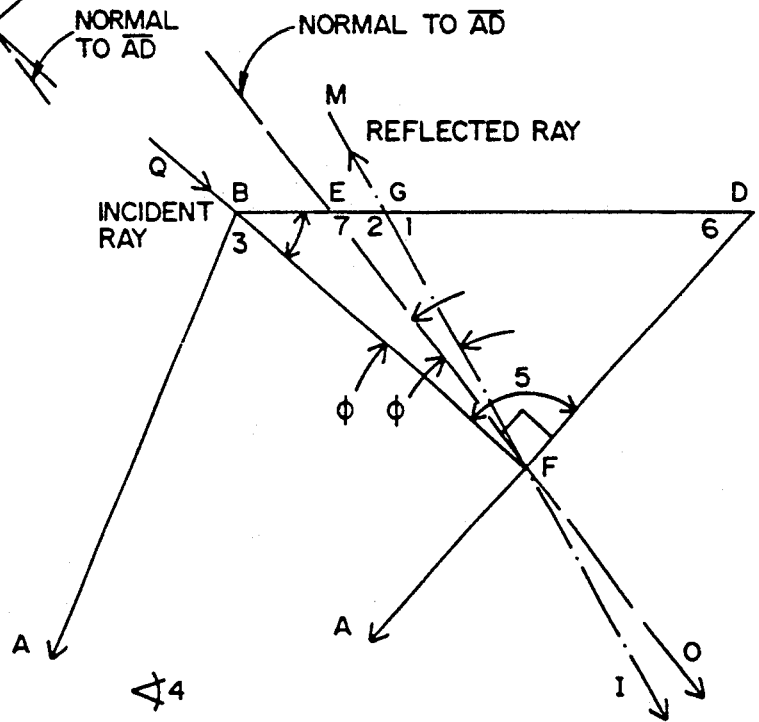

Referring now to FIGS. 4, 4a and 4b, it will be seen that the eye and the rays from the n and n+1 rings are shown schematically therein. The ray from the n ring intersects the actual surface of the eye at A which corresponds with the reference surface. No distortion is assumed at position A. The ray from the n+1 ring intersects the reference surface at B. However, it is assumed for purposes of demonstration that, due to distortion, the actual point of contact between the n+1 ring and the eye surface is at point F. The length of line BD is a measure of the bulging or flatness of the eye at that point.

The triangle ABD is shown in detail in FIG. 4b. Line AD is assumed to be the actual surface which ray QB intersects at F. Ray QB is reflected at an angle equal to the angle between QF and the normal to line AD. This angle Φ is crucial because once it is known, the value of line BD or the distortion can be determined. The length of line BD is also dependent upon the length of line AB as well as on the angles α and β which are known from the geometry of the optical system. The length AB is the distance between successive rings.

Figure 5:
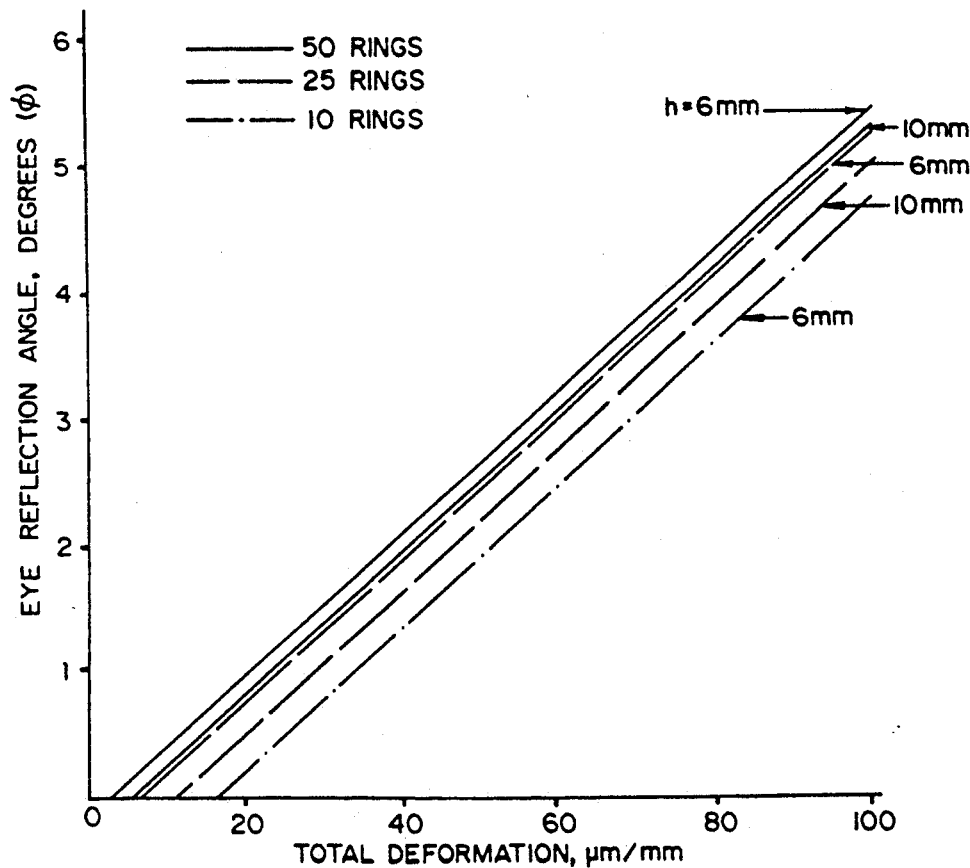
FIG. 5 is a graphical representation of expected deflection angles and actual deformation for various ring systems and viewing radii.

Examples of deflection angles for various actual deformations for different ring systems and viewing radii are shown in FIG. 5. As illustrated therein, for reticles in which there are 10, 25 and 50 rings respectively, total deformations up to 100 micrometers per millimeter produce an eye reflection angle or deflection angle Φ less than 6 degrees. Thus, the deflection angles are of the appropriate order of magnitude to be easily measured but are not large enough to escape the optical system. FIG. 5 also shows that the greater the number of rings, the greater is the deflection angle Φ for the same amount of eye deformation.

Figure 6:
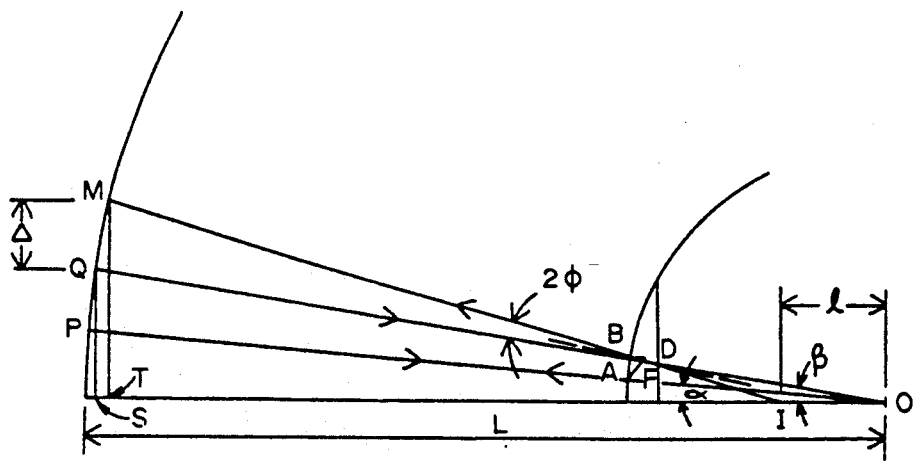
FIG. 6 is a schematic representation of a portion of the numerical process of the present invention specifically illustrating how the measured angle of deflection of laser generated rings is also dependent upon the focusing distance of the invention.
Figure 7:
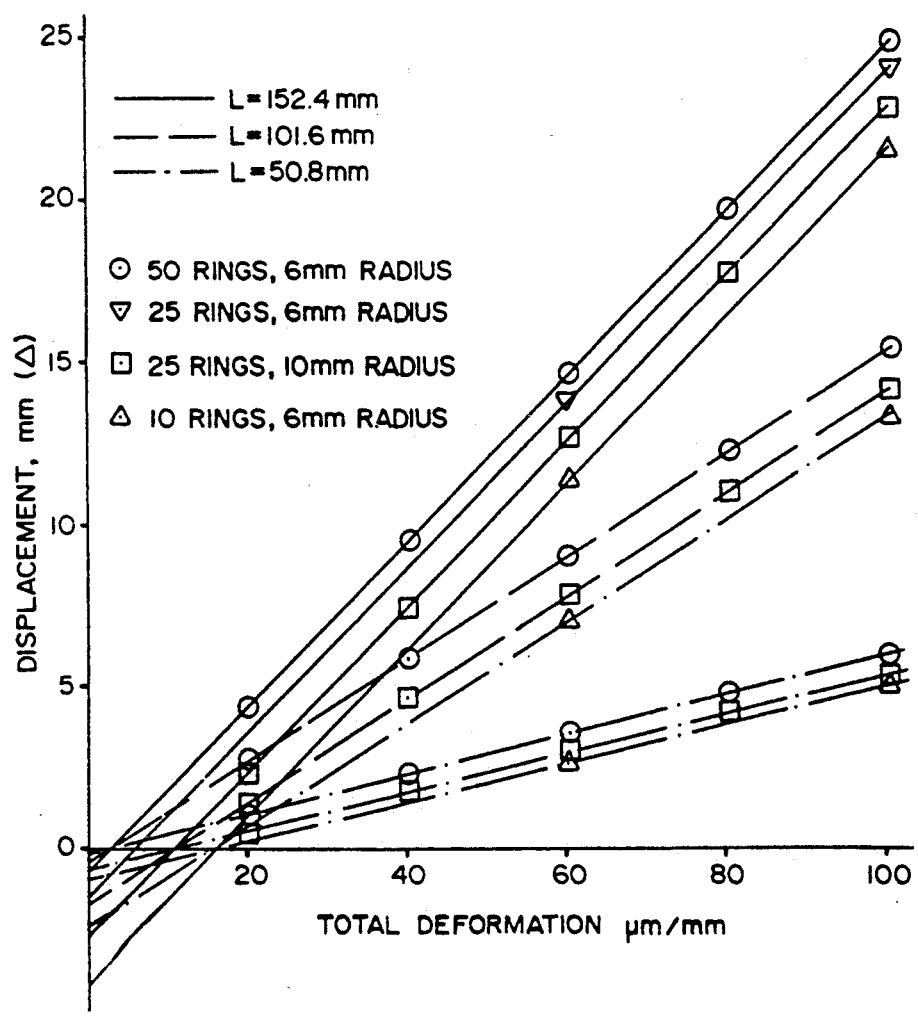
FIG. 7 is a graphical representation illustrating the relationship between vertical displacement on the focusing lens and total deformation for various ring geometries and focusing distances.

FIG. 6 demonstrates how the deflection angle Φ corresponds to a vertical displacement on the focusing lens. Displacement is the difference between incident and reflected rays measured vertically on the focusing lens and is also dependent on the focusing distance L. The graph of FIG. 7 shows vertical displacement Δ as it varies with total deformation or the various ring geometries shown in FIG. 5 as well as for different focusing distances L. As seen in FIG. 7, the larger the focusing distance L, the greater is the displacement for all ring geometries. Also seen in FIG. 7, for two geometries having the same number of rings, the one with the smaller viewing radius produces the greater displacement. It is preferable to choose a focusing distance and a ring geometry which will prevent the displaced rays from escaping the optical limits of the system and which will also avoid the necessity for requiring larger and more expensive optics.

Figure 8:
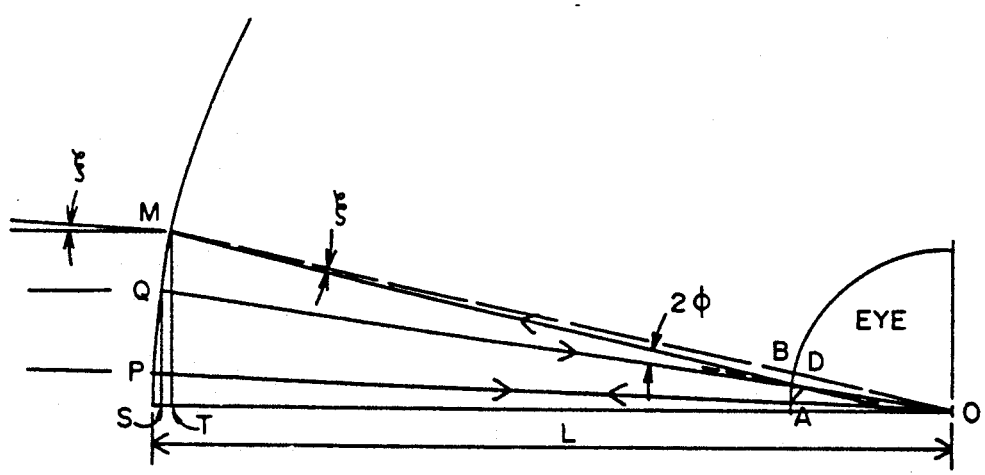
FIG. 8 is an additional schematic diagram illustrating the behavior of certain rays of the apparatus of the present invention.

Referring again to FIG. 6 it will be seen that the reflected ray FM, if projected back towards the center of the eye, crosses the central horizontal ray at some distance from the focus. Because ray IM does not originate at the focus, it will not be reflected back from the focusing lens in a horizontal line as would ray AP or ray BQ. Consequently, this will cause the reflected ray to diverge slightly from the horizontal at M. This diverging angle $\xi$ is shown in FIG. 8. This diverging angle can be approximated as equal to the angle made by the ray MF and ray MO where MO is the ray drawn from point M to the focus of the eye. This angle adds additional displacement from the incident ray, but should be kept small to keep all rays within the limits of the optical system.

Figure 9:
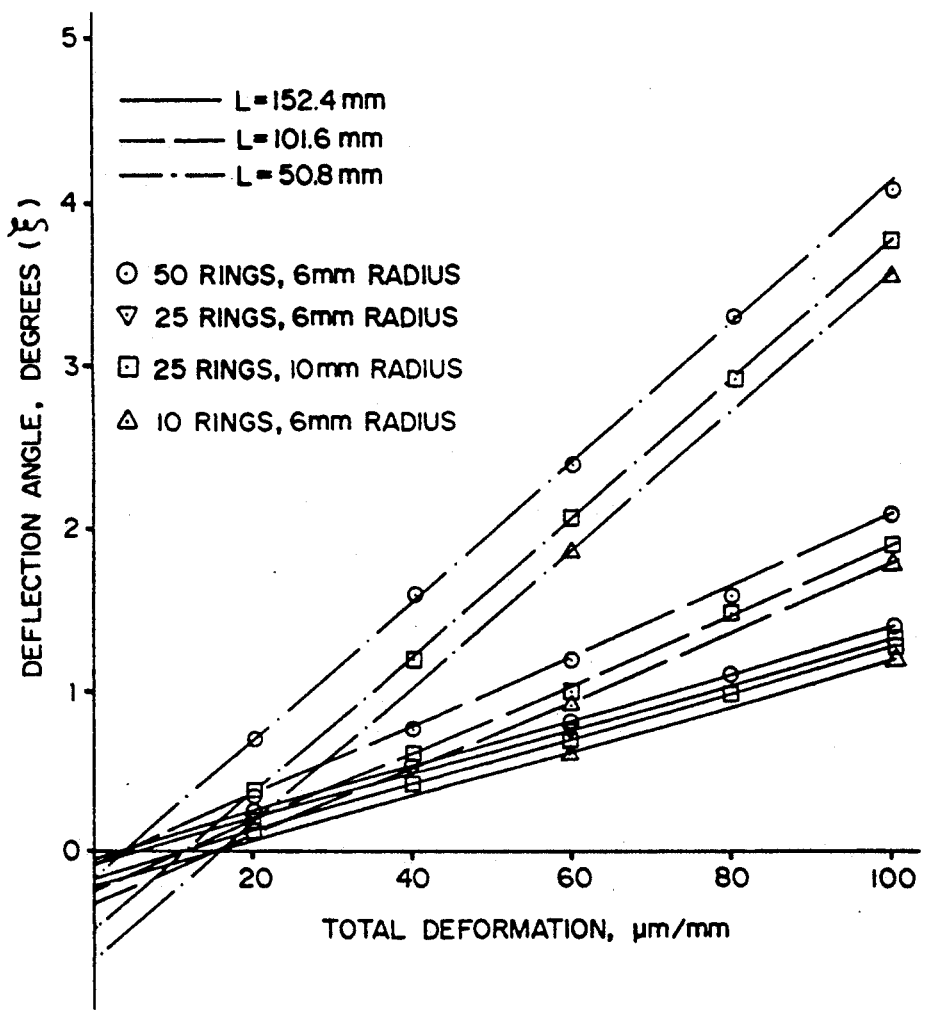
FIG. 9 is a graphical representation illustrating the relationship between the deflection angle and eye deformation for various ring systems and lens distances.

In this regard, FIG. 9 illustrates this diverging angle $\xi$ as it varies with total deformation for the previously indicated ring system and lens distances. FIG. 9 illustrates that although the longer distances yield higher displacement values, they also produce higher diverging angles. FIGS. 5, 7 and 9 together demonstrate how an actual eye surface, which differs from a reference surface, will give rise to a reflected ray which is displaced from the incident ray on the focusing lens. This displacement is a function of the geometry of the system and its difference from the true surface. In an actual measurement using the present invention, the displacement and deflection angles are measured quantities and the reflection angle and the deformation are generated based upon the following formulas.

$$\Theta = \arcsin(h/r)$$
$$H = L * \tan \Theta$$
$$\eta = \Theta/(\text{Number of Rings})$$
$$\alpha = N * \eta$$
$$\beta = (N+1) * \eta$$
$$h_1 = r * \sin \alpha$$
$$h_2 = r * \sin \beta$$
$$\gamma = \frac{1}{2}(\alpha + \beta)$$
$$\text{Ring Spacing} = h_2 - h_1$$
$$\delta = \text{Total Deformation} * \text{Ring Spacing}$$
$$AB = [2 * r^2 (1 - \cos\eta)]^{\frac{1}{2}}$$
$$AD = [AB^2 + \delta^2 - 2 * AB * \delta * \cos(90+\gamma)]^{\frac{1}{2}}$$
$$\angle 6 = \arcsin[(AB/AD)\sin(90° + \gamma)]$$
$$\angle 5 = 180° - (\angle 6 + \beta)]$$
$$\Phi = 90° - \angle 5$$
$$\Delta = MT - QS$$
$$QS = L * \sin\beta$$
$$MT = MI * \sin(2 * \Phi + \beta)$$
$$MI = MF + FI$$
$$FI = (\lambda * \sin\beta)/\sin(2 *\Phi) \text{ where } \lambda = FO * \sin(2 *\Phi)$$
$$\sin(180° - (2 *\Phi + \beta))$$
and
$$FO = r - \delta \sin_\angle 6$$
$$\sin(90° + \Phi)$$
$$MF = MG + GF$$
Since GF << MG, then MF = MG
$$MG = L - r$$
$$\xi = 2 * \Phi + \beta - \arcsin(MT/L)$$

The computer software for carrying out the numerical analysis in accordance with the equations above for measured deflection angles and displacement is provided herein in Table II.

TABLE II

List of POLYCOR2.BAS

```
10      REM POLYNOMIAL REGRESSION FOR THE CORNEA TASK
20      DIM C(50), B(50)
30      FOR I=1 TO 5
40      C(I)=0
50      B(I)=0
60      NEXT I
70      FOR I=6 TO 36
80      C(I)=0
90      NEXT I
100     B(1)=1
110     W=0:N=0:S1=0:S2=0:S3=0:S4=0:S5=0
120     PRINT "MAX. DEGREE= ";
130     INPUT D2:LPRINT
140     LPRINT "MAX DEGREE = ";D2
150     LPRINT
160     PRINT "MAX NO. POINTS";
170     INPUT Q
180     LPRINT
190     PRINT "ENTER DATA";
200     LPRINT "DATA USED":LPRINT
210     IF W=0 THEN 230
220     PRINT "NOT ALLOWED";
```

```
230    IF N<>0 THEN 270
240    LPRINT "NO.";
250    LPRINT TAB(16);"X"
260    LPRINT TAB(30);"Y"
270    PRINT "X=? , Y=";
290    INPUT B(2) , Y
300    LPRINT N+1 , B(2) , Y
310    Z=1
320    FOR I=2 TO D2
330    B(I+1)=B(I)*B(2)
340    NEXT I
350    B(D2+2)=Y
360    R=0
370    FOR I=1 TO D2+2
380    FOR J=I TO D2+2
390    R=R+1
400    C(R)=C(R)+B(I)*B(J)*Z
410    NEXT J
420    NEXT I
430    S1=S1 + B(2)*Z
440    S2=S2+B(2)^2*Z
450    S3=S3 + Y*Z
460    S4=S4 + Y*Y*Z
470    S5=S5+B(2)*Y*Z
480    N=N+Z
490    IF N=Q THEN 510
500    GOTO 270
510    IF N<=D2-W THEN 890
520    PRINT "HOW MANY COEF.; MUST LESS THAN MAX NO. OF DEG. =";
530    INPUT D1
540    LPRINT
550    LPRINT "NO.COEF. REQ. =";D1
560    IF D1<D2-W THEN 580
570    PRINT "MAX DEG =";D2-W
580    IF W=0 THEN 880
590    T=0
600    FOR I=1 TO D1+1
610    B(I)=0
620    FOR J=1 TO D1-I+2
630    R=(I+J-1)*(D2+2-.5*(I+J))
640    B(I)=B(I)+C(T+J)*C(R)
650    NEXT J
660    T=I*(D2+(3-I)/2)
670    NEXT I
680    R1=0
690    FOR I=2 TO D1+1
700    R1=R1+C(I*(D2+(3-I)/2))^2
710    NEXT I
720    T0=C((D2+1)*(D2+2)/2)
730    T0=T0-C(D2+1)^2
740    LPRINT
750    LPRINT "COEFFICIENTS"
760    LPRINT
770    REM
780    FOR I=1 TO D1+1
790    LPRINT "B(";I-1;") =";
800    LPRINT USING "##.###^^^^";B(I)
810    NEXT I
820    LPRINT
```

```
830     LPRINT
840     LPRINT "R SQUARE =";
850     LPRINT USING "##.###^^^^";R1/T0
860     LPRINT
870     GOTO 1330
880     IF N>D2 THEN 900
890     PRINT "NOT ENOUGH POINTS";
900     P=1
910     W=1
920     D2=D2+1
930     FOR J=1 TO D2
940     IF C(P)>=0 THEN 970
950     LPRINT "MATRIX UNSTABLE - USE LOWER MAX. DEGREE !"
960     LPRINT
970     C(P)=SQR(C(P))
980     FOR I=1 TO D2-J+1
990     C(P+I)=C(P+I)/C(P)
1000    NEXT I
1010    R=P+I
1020    S=R
1030    FOR L=1 TO D2-J
1040    P=P+1
1050    FOR M=1 TO D2+2-J-L
1060    C(R+M-1)=C(R+M-1)-C(P)*C(P+M-1)
1070    NEXT M
1080    R=R+M-1
1090    NEXT L
1100    P=S
1110    NEXT J
1120    T=(D2+1)*(D2+2)/2
1140    FOR I=1 TO D2-1
1150    T=T-1-I
1160    C(T)=1/C(T)
1170    FOR J=1 TO D2-I
1180    P=D2+1-I-J
1190    P=P*(D2+1-(P-1)/2)-I
1200    R=P-J
1210    S=0
1220    U=I+J+1
1230    V=P
1240    FOR K=1 TO J
1250    V=V+U-K
1260    S=S-C(R+K)*C(V)
1270    NEXT K
1280    C(P)=S/C(R)
1290    NEXT J
1300    NEXT I
1310    C(1)=1/C(1)
1320    GOTO 570
1330    LPRINT
1340    LPRINT "                    STATISTICS"
1350    LPRINT
1360    S8=SQR((S2-S1^2/N)/(N-1))
1370    S9=SQR((S4-S3^2/N)/(N-1))
1380    R9=(S5-S1*S3/N)/(N-1)/S8/S9
1390    LPRINT
1400    LPRINT "NO. POINTS = ";N
1410    LPRINT
1420    LPRINT "X: MEAN = ";
```

```
1430    LPRINT USING "##.###^^^^";S1/N;
1440    LPRINT TAB(25);"STD DEV =";
1450    LPRINT USING"##.###^^^^";S8
1460    LPRINT"Y: MEAN =";
1470    LPRINT USING "##.###^^^^";S3/N
1480    LPRINT TAB(25);"STD DEV =";
1490    LPRINT USING "##.###^^^^";S9
1500    LPRINT
1510    LPRINT "CORR COEFF =";
1520    LPRINT USING "##.###^^^^";R9
1530    LPRINT
1540    PRINT "DO YOU WANT TO DO ESTIMATE, TABLE, OR STOP.
1550    INPUT G$
1560    IF G$="E" THEN 1590
1570    IF G$="T" THEN 1650
1580    IF G$="S" THEN 1810
1590    LPRINT "              ESTIMATE"
1600    PRINT "X=";
1610    INPUT A
1620    B(I)=A
1630    C(I)=1
1640    GOTO 1690
1650    LPRINT "              TABLE"
1660    PRINT
1670    PRINT "XMIN,XMAX,STEP=";
1680    INPUT A,B(I),C(I)
1690    LPRINT
1700    FOR I=A TO B(I) STEP C(I)
1710    Y=B(D1+1)
1720    FOR J=D1 TO 1 STEP -1
1730    Y=Y*I+B(J)
1740    NEXT J
1750    LPRINT "X=";
1760    LPRINT USING "##.###^^^^";I;
1770    LPRINT TAB(20);"Y=";
1780    LPRINT USING "##.###^^^^";Y
1790    NEXT I
1800    GOTO 1540
1810    STOP
1820    END
```

List of CURSOR59.BAS

```
10     REM FIRST CONT.DIGITIZE THEN FREEZE
20     REM
30     REM MOVE CURSOR ROUTINE
40     REM
50     OUT 164,INIT
60     FOR I=1 TO 2
70     WAIT &HA4,2,2
80     OUT &HA2,&H10
90     OUT &HA3,&H00
100    WAIT &HA4,2,2
110    OUT &HA2,&H0B
120    OUT &HA3,&H00
130    WAIT 164,2,2
140    OUT &HA2,&H38
150    OUT &HA3,&H00
```

```
160     WAIT &HA4,2,2
170     OUT &HA0,&H01
180     OUT &HA1,&H00
190     WAIT &HA4,2,2
200     OUT &HA2,&H3D
210     OUT &HA3,&H00
220     WAIT &HA4,2,2
230     OUT &HA0,&H01
240     OUT &HA1,&H00
250     WAIT &HA4,2,2
260     OUT &HA2,&H39
270     OUT &HA3,&H00
280     NEXT I
290     REM
300     REM CURSOR DISPLAY
310     REM
320     WAIT &HA4,2,2
330     OUT &HA2,26
340     OUT &HA3,0
350     WAIT &HA4,2,2
360     OUT &HA2,27
370     OUT &HA3,0
380     WAIT &HA4,2,2
390     OUT &HA0,1
400     OUT &HA1,0
410     T=0
420     INPUT "",MOV$
430     if mov$="1" then 440 else 490
440     M=0
450     X=0
460     Y=1
470     N=0
480     GOTO 1380
490     if mov$="11" then 500 else 550
500     m=0
510     x=0
520     y=10
530     n=0
540     goto 1380
550     if mov$="2" then 560 else 610
560     M=0
570     X=0
580     Y=&HFF
590     N=&HFF
600     goto 1380
610     if mov$="22" then 620 else 670
620     m=0
630     x=0
640     y=&Hf6
650     n=&HFF
660     goto 1380
670     if mov$="3" then 680 else 730
680     M=0
690     X=1
700     Y=0
710     N=0
720     GOTO 1380
730     if mov$="33" then 740 else 790
740     m=0
```

```
750     x=10
760     y=0
770     n=0
780     goto 1380
790     if mov$="4" then 800 else 850
800     M=&HFF
810     X=&HFF
820     Y=0
830     N=0
840     GOTO 1380
850     if moV$="44" then 860 else 910
860     m=&HFF
870     x=&HF6
880     y=0
890     n=0
900     goto 1380
910     if mov$="5" then 920 else 970
920     M=0
930     X=1
940     Y=1
950     N=0
960     GOTO 1380
970     if mov$="55" then 980 else 1030
980     m=0
990     x=10
1000    y=10
1010    n=0
1020    goto 1380
1030    if mov$="6" then 1040 else 1090
1040    M=&HFF
1050    X=&HFF
1060    Y=&HFF
1070    N=&HFF
1080    GOTO 1380
1090    if mov$="66" then 1100 else 1150
1100    M=&HFF
1110    x=&HF6
1120    y=&hF6
1130    N=&HFF
1140    goto 1380
1150    if mov$="7" then 1160 else 1210
1160    M=&HFF
1170    X=&HFF
1180    Y=1
1190    N=0
1200    GOTO 1380
1210    if mov$="77" then 1220 else 1270
1220    M=&HFF
1230    x=&hF6
1240    y=10
1250    n=0
1260    goto 1380
1270    if mov$="8" then 1280 else 1330
1280    M=0
1290    X=1
1300    Y=&HFF
1310    N=&HFF
1320    goto 1380
1330    if mov$="88" then 1340 else 1470
```

```
1340    M=0
1350    x=10
1360    y=&Hf6
1370    n=&HFF
1380    WAIT &HA4,2,2
1390    OUT &HA2,25
1400    OUT &HA3,0
1410    WAIT &HA4,2,2
1420    OUT &HA0,X
1430    OUT &HA1,M
1440    WAIT &HA4,2,2
1450    OUT &HA0,Y
1460    OUT &HA1,N
1470    IF MOV$="N" THEN 1480 ELSE 1640
1480    wait &Ha4,2,2
1490    OUT &HA2,124
1500    OUT &HA3,0
1510    WAIT &HA4,1,0
1520    DX=INP(160)
1530    DX1=INP(161)
1540    IF DX1=255 THEN 1550 ELSE 1570
1550    DX1=DX1-256
1560    DX=DX-256
1570    WAIT &HA4,1,0
1580    DY=INP(160)
1590    DY1=INP(161)
1600    IF DY1=255 THEN 1610 ELSE 1630
1610    DY1=DY1-256
1620    DY=DY-256
1630    PRINT TAB(20);DX,TAB(40);DY
1640    IF MOV$="F" THEN 1650 ELSE 420
1650    rem
1660    rem set cursor location as new coordinate origin
1670    rem
1680    wait &Ha4,2,2
1690    out &HA2,23
1700    out &HA3,0
1710    wait &HA4,2,2
1720    OUT &HA0,DX
1730    OUT &HA1,DX1
1740    WAIT &HA4,2,2
1750    OUT &HA0,DY
1760    OUT &HA1,DY1
1770    wait &HA4,2,2
1780    OUT &HA2,124
1790    out &Ha3,0
1800    wait &Ha4,1,0
1810    XORIGN=INP(&HA0)
1820    XORIGN1=INP(&HA1)
1830    WAIT &HA4,1,0
1840    YORIGN=INP(&HA0)
1850    YORIGN1=INP(&HA1)
1860    PRINT TAB(20);XORIGN;TAB(30);YORIGN
1870    OPEN "R", #1, "TOPODATA", 100
1880    INPUT "",MOV$
1890    if mov$="1" then 1900 else 1950
1900    M=0
1910    X=0
1920    Y=1
```

```
1930  N=0
1940  GOTO 2860
1950  if mov$="11" then 1960 else 2010
1960  m=0
1970  x=0
1980  y=10
1990  n=0
2000  goto 2860
2010  if mov$="2" then 2020 else 2070
2020  M=0
2030  X=0
2040  Y=&HFF
2050  N=&HFF
2060  goto 2860
2070  if mov$="22" then 2080 else 2130
2080  m=0
2090  x=0
2100  y=&Hf6
2110  n=&HFF
2120  goto 2860
2130  if mov$="3" then 2140 else 2190
2140  M=0
2150  X=1
2160  Y=0
2170  N=0
2180  GOTO 2860
2190  if mov$="33" then 2200 else 2250
2200  m=0
2210  x=10
2220  y=0
2230  n=0
2240  goto 2860
2250  if mov$="4" then 2260 else 2310
2260  M=&HFF
2270  X=&HFF
2280  Y=0
2290  N=0
2300  GOTO 2860
2310  if moV$="44" then 2320 else 2370
2320  m=&HFF
2330  x=&HF6
2340  y=0
2350  n=0
2360  goto 2860
2370  if mov$="5" then 2380 else 2430
2380  M=0
2390  X=1
2400  Y=1
2410  N=0
2420  GOTO 2860
2430  if mov$="55" then 2440 else 2490
2440  m=0
2450  x=10
2460  y=10
2470  n=0
2480  goto 2860
2490  if mov$="6" then 2500 else 2550
2500  M=&HFF
2510  X=&HFF
```

```
2520    Y=&HFF
2530    N=&HFF
2540    GOTO 2860
2550    if mov$="66" then 2560 else 2630
2560    M=&HFF
2570    x=&hF6
2580    PRINT TAB(50);X
2590    y=&hF6
2600    PRINT TAB(55);Y
2610    N=&HFF
2620    goto 2860
2630    if mov$="7" then 2640 else 2690
2640    M=&HFF
2650    X=&HFF
2660    Y=1
2670    N=0
2680    GOTO 2860
2690    if mov$="77" then 2700 else 2750
2700    M=&HFF
2710    x=&hF6
2720    y=10
2730    n=0
2740    goto 2860
2750    if mov$="8" then 2760 else 2810
2760    M=0
2770    X=1
2780    Y=&HFF
2790    N=&HFF
2800    goto 2860
2810    if mov$="88" then 2820 else 2970
2820    M=0
2830    x=10
2840    y=&Hf6
2850    n=&HFF
2860    WAIT &HA4,2,2
2870    OUT &HA2,25
2880    OUT &HA3,0
2890    WAIT &HA4,2,2
2900    OUT &HA0,X
2910    PRINT X
2920    OUT &HA1,M
2930    WAIT &HA4,2,2
2940    OUT &HA0,Y
2950    PRINT Y
2960    OUT &HA1,N
2970    IF MOV$="R" THEN 3140 ELSE 2980
2980    wait &Ha4,2,2
2990    OUT &HA2,124
3000    OUT &HA3,0
3010    WAIT &HA4,1,0
3020    DX=INP(160)
3030    DX1=INP(161)
3040    IF DX1=255 THEN 3050 ELSE 3070
3050    DX1=DX1-256
3060    DX=DX-256
3070    WAIT &HA4,1,0
3080    DY=INP(160)
3090    DY1=INP(161)
3100    IF DY1=255 THEN 3110 ELSE 3130
```

```
3110  DY1=DY1-256
3120  DY=DY-256
3130  PRINT
3140  INPUT "DO YOU WANT CURSOR POSITION RECORDED (Y/N)";Q$
3150  IF Q$="Y" THEN 3170 ELSE 1880
3160  R0=SQR(RX0^2+RY0^2)
3170  GOSUB 3660
3180  INPUT "NEXT DATA POINT PAIR OR (E) TO EXIT";R$
3190  IF R$="E" THEN 3210 ELSE 3200
3200  GOTO 1880
3210  GOSUB 3750
3220  FOR T=1 TO T
3230  GET #1,T
3240  R1X0=CVI(R1X0$)
3250  RX0=CVI(RX0$)
3260  R1Y0=CVI(R1Y0$)
3270  RY0=CVI(RY0$)
3280  R0=SQR(RX0^2+RY0^2)
3290  CALF=0.4666
3300  ROMM=R0*CALF
3310  PRINT TAB(30);ROMM
3320  NEXT T
3330  WAIT &HA4,2,2
3340  OUT &HA2,124
3350  OUT &HA3,0
3360  WAIT &HA4,1,0
3370  DX=INP(160)
3380  DX1=INP(161)
3390  WAIT &HA4,1,0
3400  DY=INP(160)
3410  DY1=INP(161)
3420  WAIT &HA4,2,2
3430  OUT &HA2,25
3440  OUT &HA3,0
3450  WAIT &HA4,2,2
3460  PRINT
3470  PRINT "DX IS = ";DX
3480  PRINT "DX1 IS = ";DX1
3490  PRINT "DY IS = ";DY
3500  PRINT "DY1 IS = ";DY1
3510  DX=256-DX
3520  DX1=255
3530  OUT &HA0,DX
3540  OUT &HA1,DX1
3550  WAIT &HA4,2,2
3560  DY=256-DY
3570  DY1=255
3580  PRINT DX
3590  PRINT DX1
3600  PRINT DY
3610  PRINT DY1
3620  OUT &HA0,DY
3630  OUT &HA1,DY1
3640  GOTO 1880
3650  CLOSE:END
3660  FIELD #1, 20 AS R1X0$, 20 AS RX0$, 20 AS R1Y0$, 20 AS RY0$
3670  T=T+1
3680  PRINT "T IS NOW =   ";T
3690  LSET R1X0$=MKI$(DX1)
```

```
3700  LSET RX0$=MKI$(DX)
3710  LSET R1Y0$=MKI$(DY1)
3720  LSET RY0$=MKI$(DY)
3730  PUT #1,T
3740  RETURN
3750  PRINT TAB(30);"FRINGE RADII"
3760  PRINT
3770  IF MOV$="3" THEN 3790 ELSE 3780
3780  IF MOV$="33" THEN 3790 ELSE 3820
3790  PRINT TAB(31);"AZIMUTH 0"
3800  PRINT
3810  GOTO 3220
3820  IF MOV$="4" THEN 3840 ELSE 3860
3830  IF MOV$="44" THEN 3840 ELSE 3860
3840  PRINT TAB(20);"AZIMUTH 180"
3850  PRINT
3860  IF MOV$="1" THEN 3880 ELSE 3910
3870  IF MOV$="11" THEN 3880 ELSE 3910
3880  PRINT TAB(31);"AZIMUTH 90"
3890  PRINT
3900  GOTO 3220
3910  IF MOV$="2" THEN 3930 ELSE 3920
3920  IF MOV$="22" THEN 3930 ELSE 3960
3930  PRINT TAB(31);"AZIMUTH 270"
3940  PRINT
3950  GOTO 3220
3960  IF MOV$="5" THEN 3980 ELSE 3970
3970  IF MOV$="55" THEN 3980 ELSE 4010
3980  PRINT TAB(31);"AZIMUTH 45"
3990  PRINT
4000  GOTO 3220
4010  IF MOV$="6" THEN 4030 ELSE 4020
4020  IF MOV$="66" THEN 4030 ELSE 4060
4030  PRINT TAB(31);"AZIMUTH 225"
4040  PRINT
4050  GOTO 3220
4060  IF MOV$="7" THEN 4080 ELSE 4070
4070  IF MOV$="77" THEN 4080 ELSE 4110
4080  PRINT TAB(31);"AZIMUTH 135"
4090  PRINT
4100  GOTO 3220
4110  IF MOV$="8" THEN 4130 ELSE 4120
4120  IF MOV$="88" THEN 4130 ELSE 4150
4130  PRINT TAB(31);"AZIMUTH 315"
4140  PRINT
4150  RETURN
```

It will now be understood that what has been disclosed herein comprises a laser beam keratometer having only one optical reticle. The keratometer provides an optical subsystem designed to impose a series of rings generated by a reticle on the surface of the eye and to capture a series of reflected rings from the eye. The image of reflected rings is transmitted to a computer which effectively superimposes a computer stored reference image on the image reflected from a subject's eye. Data processing numerical analysis then provides a real time display or numerical information on the condition of the eye. When no deformation exists there is no displacement of the rings from the reference set stored in the computer. However, any deformation that is observed causes some or all of the rings to be displaced slightly from the reference set and the computer analyzes the amount of deformation to produce either a detailed topology of the eye or a simpler numerical representation of the eye's refractive condition. The real time or near real time capabilities of the present invention are particularly advantageous for use in medical diagnosis and evaluation of the corneal contour for eye surgery as well as for evaluation of the corneal contour post-operatively. The present system provides corneal contour evaluation over a much larger surface area than previously possible using prior art keratometers. Furthermore, the novel use of one reticle-produced image, the eye's reflection of which is compared against a reference image in a computer, alleviates prior art alignment problems and resulting fringes.

Those having skill in the art to which the present invention pertains will now, as a result of the disclosure herein, perceive various modifications and additions which may be made to the invention. Thus for example, while FIG. 1 demonstrates an illustrative embodiment of an apparatus configured to accomplish the method of the invention, it will be understood that other optical subsystems may be utilized to generate the reflected image used by the computer in calculating the deformation and surface characteristics of the cornea. Furthermore, while it will be observed that a particular reticle geometry has been used herein, other reticle geometries and corresponding modified numerical analyses may be readily employed to accomplish essentially the same method as disclosed herein or a method substantially equivalent thereto. Consequently, it will be understood that all such modifications and additions are contemplated as being within the scope of the invention which is to be limited only by the claims appended hereto.

We claim:

1. An apparatus for measuring the shape of a cornea, the apparatus of the type having a source of light and an optical assembly for focusing said light onto the cornea and for directing reflected light from the cornea onto an imaging device; the apparatus comprising:
   a single reticule for interrupting a portion of said light to form a selected pattern on the cornea, said pattern being deformable by an irregularly shaped cornea as said pattern is reflected by the cornea and appears on said imaging device; and,
   means for measuring the deformation of said reflected patern and for determining the shape of the cornea therefrom, said measuring and determining means comprising a digital computer programmed to compare said reflected pattern with a reference pattern stored in said computer, said programmed digital computer automatically aligning said reflected pattern with said reference pattern prior to calculating differences therebetween for quantitatively characterizing said shape of said cornea.

2. The apparatus recited in claim 1 wherein said reticle pattern comprises a series of concentric rings.

3. The apparatus recited in claim 2 wherein the number of rings in said reticle pattern is in the range of 10 to 50.

4. The apparatus recited in claim 2 wherein the radius of said reticle pattern is less than four inches.

5. The apparatus recited in claim 1 wherein said source of light is a laser.

6. The apparatus recited in claim 5 wherein said laser is a Helium-Neon laser.

7. The apparatus recited in claim 1 wherein said imaging device is a video camera.

8. The apparatus recited in claim 7 wherein said video camera is of the type having a solid state imaging sensor.

9. The apparatus recited in claim 8 wherein said sensor is a charge coupled device.

10. The apparatus recited in claim 1 wherein said reference pattern corresponds to a regularly shaped cornea.

11. The apparatus recited in claim 1 wherein said computer is programmed to measure the vertical distance at the focusing assembly and the angle between the incident and reflected points of said pattern and derive therefrom the angle between the irregular surface normal and the regular surface normal and the horizontal distance between the actual and reference points at the cornea.

12. A method of measuring the shape of the cornea of a subject's eye, the method comprising the steps of:
   (a) focusing a selected pattern of light on he cornea for reflection of said pattern therefrom;
   (b) focusing the reflected pattern on an imaging sensor for generating an electrical signal representation of said reflected pattern;
   (c) transferring said representation of said reflected pattern to a computer having stored therein a pattern representation of a non-deformed cornea;
   (d) automatically aligning said representation of said reflected pattern with said stored pattern representation of a non-deformed cornea by determining a center point for said reflected pattern and effectively superimposing a corresponding center point of said stored pattern representation of a non-deformed cornea for calculating any differences between said reflected pattern representation and said non-deformed cornea pattern representation relative to said superimposed center points; and,
   (e) calculating the deformation of subject's cornea based upon said calculated differences between said reflected pattern representation and said non-deformed cornea pattern representation.

13. The method recited in claim 12 wherein in step (a) said selected pattern is generated by transmitting light, emitted by a source, through a reticle.

14. The method recited in claim 12 further comprising the step of displaying an image representing the shape of the subject's cornea.

15. The method recited in claim 12 wherein said measuring step comprises the steps of measuring the vertical distance between corresponding points on said pattern representations at a focusing plane spaced from the cornea and measuring the angle between rays passing through said corresponding points.

16. The method recited in claim 15 wherein said calculating step comprises the steps of solving equations based upon said measuring steps to calculate the angle between the corresponding normals to the subject's cornea surface and the non-deformed cornea surface and to calculate the horizontal distance between corresponding points on the subject's cornea surface and the non-deformed cornea surface.

* * * * *